United States Patent
Kakiguchi et al.

(10) Patent No.: US 6,770,296 B2
(45) Date of Patent: Aug. 3, 2004

(54) PROCESS FOR PRODUCING COATED PREPARATION AND ITS USE

(75) Inventors: Yoshitomi Kakiguchi, Kawabe-gun (JP); Kunihiko Yokota, Osaka (JP); Masaru Miyawaki, Ibaraki (JP)

(73) Assignee: BASF Aktiengesellschaft, Ludwigshafen (DE)

(*) Notice: Subject to any disclaimer, the term of this patent is extended or adjusted under 35 U.S.C. 154(b) by 0 days.

(21) Appl. No.: 10/245,123

(22) Filed: Sep. 17, 2002

(65) Prior Publication Data

US 2003/0091648 A1 May 15, 2003

Related U.S. Application Data

(62) Division of application No. 09/542,929, filed on Apr. 4, 2000, now Pat. No. 6,485,742.

(30) Foreign Application Priority Data

Apr. 5, 1999 (JP) ............................................. 11-97525
May 19, 1999 (JP) .......................................... 11-138587
Mar. 15, 2000 (JP) .......................................... 2000-72275

(51) Int. Cl.$^7$ ............................ A61K 9/20; A61K 9/48; A61K 9/14

(52) U.S. Cl. ........................ 424/464; 424/451; 424/489

(58) Field of Search ................................ 424/464, 451, 424/489

(56) References Cited

U.S. PATENT DOCUMENTS 4,038,423 A * 7/1977 Hayward et al. ............. 426/72

FOREIGN PATENT DOCUMENTS

JP 64003118 * 1/1989
JP 2543683 * 10/1996

* cited by examiner

*Primary Examiner*—Alton N. Pryor
(74) *Attorney, Agent, or Firm*—Davidson, Davidson & Kappel, LLC

(57) ABSTRACT

There is provide a novel process for producing a coated preparation composed of a hydrophilic core material coated with a coat material selected from hydrophobic hot-melt lipid to control dissolution of the core material in water and to prevent blocking during the production thereof. In this process, the melted coat material is added dropwise to the core material with fluidizing the core material to form at least one coating layer about the core material in the presence of, or by addition of β-form seed crystals of the coat material. Further, there is provided a water-soluble vitamin preparation having an improved flavor which contains a coated water-soluble vitamin having an unpleasant flavor produced by the novel process.

2 Claims, No Drawings

PROCESS FOR PRODUCING COATED PREPARATION AND ITS USE

This application is a divisional of U.S. patent application Ser. No. 09/542,929, filed Apr. 4, 2000 now U.S. Pat. No. 6,485,742.

BACKGROUND OF THE INVENTION

1. Field of the Invention

The present invention relates to a process for producing a coated preparation. More specifically, it relates to a process for producing a coated preparation in the form of finely divided particles which is composed of a core material of a useful hydrophilic material, in particular, an organic acid or its salt, coated with one or more coating layers of a coat material selected from hydrophobic hot-melt lipid to minimize the external influence on the core material or the influence on surroundings by the core material and to improve blocking between coated particles.

Further, the present invention relates to a water-soluble vitamin preparation having an improved flavor which utilizes the process of the present invention, and its production process. More specifically, it also relates to a water-soluble vitamin preparation useful as medicines and health food in which an unpleasant flavor of a water-soluble vitamin is improved, a dissolution rate of a water-soluble vitamin in water is reduced to provide slow-release properties, reactions between components are inhibited, and preparation properties are improved, as well as its production process.

2. Disclosure of the Prior Art

Organic acids such as citric acid, fumaric acid, and sorbic acid are widely used as, for example, acidulants, pH adjusting agents, preservatives, and the like. However, in many cases, adverse influences due to low pH are observed during processing and storage of food products and the like.

In addition, the organic acid, L-ascorbic acid, is widely utilized in various food, health food, feed, medicines, and the like, for example, as a quality improving agent, an acidulant, a nutrient enhancer as vitamin C, a medicament, and the like.

In the utilization of L-ascorbic acid as a quality improving agent, its oxidative and reductive reactivity is expected. However, the reaction rate is too fast to last its improving effect for extended periods of time. On the other hand, in the utilization of L-ascorbic acid as an enhancer, it should be kept stably during production and storage of food and the like. However, it is very difficult to keep L-ascorbic acid stably, in particular, in the presence of water, oxygen, metal salts and the like, resulting in such a drawback that the desired function cannot be exhibited and, sometimes, its oxidative and reductive reactivity adversely influences another component.

Then, for solving these problems, processes for producing coated preparations have been proposed to prevent these organic acids from contact with water, oxygen and the like and to control its reactivity. In these processes, an organic acid is used as a core material and a coat of a hydrophobic material is provided about the surface of the core material. For example, a fine powder of an organic acid is coated with a hydrophobic material such as a hot-melt fat which is a solid at room temperature by a spray cooling method, a spray coating method, a rotary mixing-drying method, or the like.

In particular, for example, JP-A 63-164863, JP-A 63-164864 and JP-A 63-258813 propose a process for producing a coated preparation in which a core material such as a water-soluble vitamin powder or an organic acid powder is brought into contact with and hit by a coat material such as a fat so that the coat material adheres to the core material to cover it. JP-A 55-92661, JP-B 62-18152, JP-A 64-3118 and JP-A 64-3119 propose a process for producing a fine powder preparation in which finely divided organic particles and a melted fat are mixed at an elevated temperature and then the mixture is spray-cooled. JP-A 50-52221 proposed a process for coating organic acid particles in which fat is dissolved in a solvent and an organic acid is covered with resultant solution in a fluidized bed device with evaporating the solvent. Further, for improving the degree of covering with a coat material and solving the problem of simplicity and convenience in these processes, Japanese Patent Application No. 9-13702 (JP-A 10-203965) filed by the present assignee propose a process for producing a coated preparation in which a coat material melted with heating is continuously or intermittently added to a hydrophilic core material with mixing the core material at a temperature of the coat material to solidify the coat material to form plurality of coating layers about the core material.

However, in the above known processes, there are such problems that inhibition of dissolution of a core material such as an organic acid in water is insufficient or very difficult and, even if the dissolution can be prevented, productivity of the processes is very low from the economical view point. Moreover, there is a problem of blocking between particles coated with a hydrophobic hot-melt coat material during production steps.

OBJECTS OF THE INVENTION

One main object of the present invention is to provide a process for producing a coated preparation which can inhibit the dissolution of the core material in water and can prevent blocking between coated particles during production steps by improving covering with a coat material to solve the above problems in the prior art processes.

This object as well as other objects and advantages of the present invention will become apparent to those skilled in the art from the following description.

SUMMARY OF THE INVENTION

The present inventors have studied intensively to achieve the above object. As a result, the present inventors have found that it is necessary to accelerate β-form crystallization of one or more coating layers composed of a coat material selected from hydrophobic hot-melt liquid upon coating about a hydrophilic core material, thereby improving covering of the core material to give a coated preparation having a low degree of dissolution in water in a high yield and, at the same time, to prevent blocking during production steps of the preparation.

In addition, although, among water-soluble vitamins, there are many substances having unpleasant flavors such as peculiar vitamin odors, bitterness and the like, the present inventors also have found that these unpleasant flavors can be improved by the process of the present invention or that disclosed by the above present assignee's Japanese Patent Application No. 9-13702 (JP-A 10-203965) in combination with sweeteners. That is, sweeteners such as aspartame and the like have been used for improving unpleasant flavors of water-soluble vitamins (JP-A 60-192571, JP-A 8-208517, etc.). Further sweeteners such as aspartame and the like have been used not only for improving unpleasant flavors but also as components of various vitamin preparation (JP-A 60-19474, JP-A 9-157174, JP-A 9-95447, Japanese Patent No. 2574176, etc.). Nevertheless, surprisingly, the present inventors have found that water-soluble vitamin preparation having a further improved flavor and various improved properties can be obtained by combining the process of the present invention or that disclosed by Japanese Patent Application No. 9-13702 (JP-A 10-203965) and a sweetener such as aspartame.

Then, the present invention provides:

(1) a process for producing a coated preparation comprising a hydrophilic core material coated with a coat material selected from hydrophobic hot-melt lipid;
said process comprising adding the melted coat material dropwise to the core material with fluidizing the core material at a temperature not higher than the solidification temperature of the coat material in the presence of β-form seed crystals of the coat material to solidify the coat material to form at least one coating layer about the core material; or
adding the melted coat material dropwise to the core material with fluidizing the core material at a temperature not higher than the solidification temperature of the coat material to solidify the coat material to form at lease one coating layer about the core material, followed by adding β-form seed crystals of the coat material, for example, within 10 minutes, to accelerate β-form crystallization of the coating layer;

(2) the process according to the above (1), wherein the core material is at least one organic material selected from the group consisting of organic acids, organic acid salts and non-organic acid vitamins;

(3) the process according to the above (2), wherein the core material is L-ascorbic acid or its salt;

(4) the process according to the above (1), wherein the coat material is at least one material selected from the group consisting of fats and oils, fatty acids, fatty acid esters, their hydrogenated products and wax;

(5) the process according to the above (1), wherein the β-form seed crystals of the coat material are a part of the coated preparation prepared separately;

(6) the process according to the above (1), wherein β-form seed crystals of the coat material is prepared separately by melting the coat material and adjusting its temperature;

(7) the process according to the above (1), wherein β-form crystallization is carried out by holding the coating layer at a pre-determined temperature after formation thereof;

(8) the process according to the above (1), wherein the core material is fluidized in a temperature controllable stirring-mixing device;

(9) the process according to the above (1), wherein β-form seed crystals of the coat material is used in an amount of 0.1 to 30% by weight based on the total weight of the coated preparation; and

(10) the process according to the above (1), wherein the core materials is formulated in an amount of 50 to 97% by weight based on the total weight of the coated preparation.

According to these aspects of the present invention, the coated preparation of the hydrophilic core material having improved stability whose dissolution in water is inhibited can be simply and conveniently obtained with preventing blocking by properly selecting the coat material and its amount to be coated, i.e., the number of coating layers and the rate of addition, adding β-form seed crystals of the coat material, and properly controlling temperature to accelerate β-form crystallization of the coating layer.

The present invention further provides:

(11) a water-soluble vitamin preparation having an improved flavor which comprises a coated water-soluble vitamin component, a sweetener and an excipient; and
said coated vitamin component obtained by coating a water-soluble vitamin core material having an unpleasant flavor with at least one coating layer of a coat material selected from hydrophobic hot-melt lipid which is formed by melting, adding and solidifying the coat material with fluidizing the core material;

(12) the water-soluble vitamin preparation according to the above (11), wherein the core material is a water-soluble vitamin selected from the group consisting of calcium ascorbate, sodium ascorbate, nicotinic acid, nicotinamide, vitamin $B_1$'s, riboflavin, riboflavin phosphate sodium, pantothenic acid, sodium pantothenate and pyridoxine hydrochloride;

(13) the water-soluble vitamin preparation according to the above (12), wherein the core material is calcium L-ascorbate;

(14) the water-soluble vitamin preparation according to the above (11), wherein the coat material is at least one material-selected from the group consisting of fats and oils, fatty acids, fatty acid esters, their hydrogenated materials and wax;

(15) the water-soluble vitamin preparation according to the above (11), wherein the coating layer is crystallized in β-form crystals;

(16) the water-soluble vitamin preparation according to the above (11), wherein the water-soluble vitamin content of the coated water-soluble vitamin component is 30 to 97% by weight;

(17) the water-soluble vitamin preparation according to the above (11), wherein the sweetener is at least one material selected from the group consisting of aspartame, potassium acesulfame, sucrarose, sodium saccharin and licorice extract;

(18) the water-soluble vitamin preparation according to the above (17), wherein the sweetener content of the preparation is 0.1 to 5.0% by weight; and

(19) the water-soluble vitamin preparation according to the above (11), wherein the preparation is in the form of powder, granules, tablets or capsules.

Furthermore, the present invention provides:

(20) a process for producing a water-soluble vitamin preparation having an improved flavor which comprises the steps of:
coating a water-soluble vitamin core material having an unpleasant flavor with at least one coating layer of a coat material selected from hydrophobic hot-melt lipid which is formed by melting, adding and solidifying the coat material with fluidizing the core material to obtain a coated water-soluble vitamin component, and
compounding the coated water-soluble vitamin component with a sweetener and an excipient;

(21) a process for producing a water-soluble vitamin preparation having an improved flavor which comprises the steps of:
coating a water-soluble vitamin core material having an unpleasant flavor with at least one coating layer of a coat material selected from hydrophobic hot-melt lipid, said coating layer being formed by melting, adding and solidifying the coat material with fluidizing the core material in the presence of β-form seed crystals of the coat material, or melting, adding and solidifying the coat material with fluidizing the core material, followed by adding β-form seed crystals of the coat material to accelerate β-form crystallization of the coating layer, to obtain a coated water-soluble vitamin component, and compounding the coated water-soluble vitamin component with a sweetener and an excipient;

(22) accelerate β-form crystallization of the coating layer the process according to the above (21), wherein the β-form seed crystals of the coat material are a part of the coated water-soluble vitamin component prepared separately;

(23) the process according to the above (21), wherein β-form seed crystals of the coat material is prepared separately by melting the coat material and adjusting its temperature;

(24) the process according to the above (21), wherein β-form crystallization is carried out by holding the coating layer at a pre-determined temperature after formation thereof;

(25) the process according to the above (21), wherein β-form seed crystals of the coat material is used in an amount of 0.1 to 30% by weight based on the total weight of the water-soluble vitamin component; and

(26) the process according to the above (20) or (21), wherein the core material is fluidized in a temperature controllable stirring-mixing device.

According to the latter aspects of the present invention, a water-soluble vitamin preparation useful as medicines and health food can be obtained. In the water-soluble vitamin preparation of the present invention, an unpleasant flavor of a water-soluble vitamin is improved to reduce an unpleasant flavor in the mouth; a dissolution rate of a water-soluble vitamin in water is reduced to provide slow-release properties; reactions between components are inhibited; and preparation properties are improved.

DETAILED DESCRIPTION OF THE PREFERRED EMBODIMENTS

In the present invention, the core material is not limited to a specific one in so far as it has a hydrophilic substance having suitable particle size. Examples thereof include citric acid, fumaric acid, tartaric acid, sorbic acid, water-soluble vitamins such as L-ascorbic acid, nicotinic acid, pantothenic acid and the like, amino acids, nucleic acids, salts of these materials with alkali metals (e.g., potassium, sodium, etc.), alkaline earth metals (e.g., calcium, magnesium, etc.), hydrophilic organic acids and organic acid salts, water-soluble non-organic acid vitamins such as vitamin B's. Preferably, the core material is L-ascorbic acid or its salt.

The particle size of the core material is not limited to a specific one, but normally, the core material is used in the form of powders, granules or crystals having the average particle size is not more than 2,000 μm, preferably 10 to 1,000 μm, more preferably 40 to 1,000 μm.

The coat material is selected from hydrophobic hot-melt lipid. As such a material, an edible material having melting point of 50 to 90° C., preferably about 60 to 80° C. is desired. Examples thereof include vegetable and animal fats and oils, hydrogenated, fractionated and interesterification products thereof, fatty acids, fatty acid esters, naturally occurring vegetable, animal and mineral wax and the like.

Examples of the fats and oils include hydrogenated soybean oil, hydrogenated tallow, hydrogenated rapeseed oil, hydrogenated fish oil, hydrogenated whale oil, hydrogenated castor oil, hydrogenated sunflower oil, hydrogenated safflower oil and the like. Example of the fatty acids include those having 14 to 28 carbon atoms and melting point of about 50 to 90° C. (e.g., palmitic acid, stearic acid, behenic acid, etc.) and their esters having surfactant activity such as glycerol esters, sugar esters, sorbitol esters, propylene glycol esters and the like.

Examples of the wax includes naturally occurring edible wax such as candelilla wax, rice wax, carnauba wax, beeswax, paraffin wax and the like.

In the present invention, these coat materials can be used alone or in combination of two or more of them. Further, plural coating layers can be formed by the same coat materials or, depending upon the combination of particular coat materials, plural coating layers of difference coat materials can be formed.

The coat material can be used in an amount of 99 to 1% by weight, preferably 99 to 10% by weight, more preferably 60 to 20% by weight based on the total weight of the coated preparation. The core material can be used in an amount of 1 to 99% by weight, preferably 1 to 90% by weight, more preferably 40 to 80% by weight based on the total weight of the coated preparation.

When the amount of the coat material is too small, covering becomes insufficient. Preferably, the amount of the coat material is selected so that the core material is covered by at least 2 layers of the coat material. By forming plural coating layers, a sufficient degree of covering can be obtained to give a coated preparation of mononuclear particles having coating layers of a high fat content.

The β-form crystals to be used as the seed crystals in the present invention can be selected from the same coat material as described above whose crystal form is β-form. The β-form seed crystals can be prepared by melting lipid having the same fatty acid composition as that of the coat material or at least one coat material to be used and holding the melt at a pre-determined temperature for pre-determined time. For example, in case of hydrogenated soybean oil, the seed crystals can be prepared by holding its melt at 50 to 60° C. for 1 to 8 hours, preferably 4 to 6 hours after melting by heating to form β-form crystals.

Further, the β-form seed crystals to be used in the present invention may be a part of the coated preparation produced in a different batch or run according to the process of the present invention. For example, among the coated preparations produced, those having too small particle size, e.g., those having particle size of not more than 850 μm, or pulverized materials of the coated preparations can be used as the β-form seed crystals. The crystal form of the coated preparation to be used as the seed crystals may be β-form, β'-form or a mixture thereof.

The seed crystals is added in an amount of 0.1 to 90% by weight, preferably 1 to 50% by weight, more preferably 1 to 30% by weight based on the total weight of the coated preparation. The seed crystals can be added together with the core material or can be added when the coat material is added dropwise. Further, the seed crystals can be added after formation of the coating layers.

The process of the present invention can be carried out by using a temperature controllable stirring—mixing device in which the core material can be fluidized. This kind of device is not specifically limited in so far as the core material and the coat material can be stirred and mixed. However, in view of easy operation and efficiency, preferably, a temperature controllable screw type, ribbon type, paddle type, high-speed fluid type or rotary disk type stirring-mixing device is used. For example, a stirring-mixing device such as Microspeed Mixer (manufactured by Takara Koki), High-speed Mixer (manufactured by Fukae Kogyo), Nauter Mixer or the like can be used.

For carrying out the process of the present invention, for example, the core material and β-form seed crystals are heated to a temperature not higher than the solidification temperature of the coat material by using the above mixer. To this is added the coat material melted by heating dropwise continuously or intermittently to cover the surface of the core material with a single layer or plural annual rings-like or spiral-like layers of the coat material uniformly. The resultant mixture is cooled and held in an incubator for ten to several tens hours to warm the mixture to effect β-form crystallization. Then, the mixture is screened to obtained the coated preparation having the desired particle size. A part of the coated preparation or that having larger particle size can be used as the seed crystals for a different batch or run as it is or after pulverization.

The warming temperature and time for β-form crystallization vary depending upon production conditions. However, normally, β-form crystallization is carried out at 50 to 60° C. for 4 to 8 hours, preferably 4 to 6 hours.

In particular, the present invention is suitable for producing the coated preparation of L-ascorbic acid. For example, 60 parts by weight of L-ascorbic acid powder, granules or crystals having particle size of not more than 2,000 μm and 15 parts by weight of the seed crystals are mixed with controlling the temperature at not higher than the solidification temperature of the coat material, e.g., at 50 to 54° C. To this is added 15 to 20 parts by weight of the coat material. Addition and solidification of the coat material are repeated to cover the surface of L-ascorbic acid with plural coat layers of the coat material. The resultant mixture is cooled to about 50° C. and allowed to stand in an incubator at 50° C. for about 5 to 7 hours. Then, the mixture is screened to select the coated preparation of L-ascorbic acid having the desired particle size.

In addition, blocking is further improved, when the coated preparation of L-ascorbic acid produced separately which has been subjected to β-form crystallization is added in an amount of about 10% by weight based on the total weight of the preparation to be produced after coating of the core material, followed by allowing to stand in an incubator at 50° C. for about 5 to 7 hours. As an additive, silicon dioxide, corn starch or the like can be advantageously used in an amount of about 1% by weight based on the total weight of the preparation.

The water-soluble vitamin preparation of the present invention comprises a coated water-soluble vitamin component, a sweetener and an excipient. The coated water-soluble vitamin component is obtained by coating a water-soluble vitamin core material having an unpleasant flavor with plural coating layers of the coat material.

In the present invention, examples of the water-soluble vitamin having an unpleasant flavor which is the core material of the coated water-soluble vitamin component include calcium ascorbate, nicotinic acid, nicotinamide, vitamin $B_1$'s (e.g., hydrochloride, nitrate, dibenzoyl thiamin, dibenzyol thiamin hydrochloride, etc.), riboflavin and its phosphate sodium, pantothenic acid, sodium pantothenate, calcium pantothenate and pyridoxine hydrochloride. Among them, calcium L-ascorbate is used.

Coating of the core material can be carried out according to the same manner as that of the above process of the present invention except that β-form seed crystals are not used. That is, the coating can be carried by adding the coat material melted by heating to the core material continuously or intermittently with fluidizing the core material at a temperature not higher than the solidification temperature of the coat material to solidify the coat material to form plural coating layers about the core material.

In addition, the coating can be carried out according to the above process of the present invention. That is, the coating can be carried out by adding the melted coat material dropwise to the core material with fluidizing the core material at a temperature not higher than the solidification temperature of the coat material in the presence of β-form seed crystals of the coat material to solidify the coat material to form at least one coating layer about the core material; or by adding the melted coat material dropwise to the core material with fluidizing the core material at a temperature not higher than the solidification temperature of the coat material to solidify the coat material to form at least one coating layer about the core material, followed by adding β-form seed crystals of the coat material to accelerate β-form crystallization of the coating layer.

In case of the coated water-soluble vitamin component, the coat material can be used in an amount of 99 to 1% by weight, preferably 99 to 10% by weight, more preferably 70 to 20% by weight based on the total weight of the coated water-soluble vitamin component. The core material can be used in an amount of 1 to 99% by weight, preferably 1 to 97% by weight, more preferably 40 to 97% by weight based on the total weight of the coated water-soluble vitamin component. When the amount of the coat material is too small, covering becomes insufficient. Preferably, the amount of the coat material is selected so that the core material is covered by at least 2 layers of the coat material. By forming plural coating layers, a sufficient degree of covering can be obtained to give a coated water-soluble vitamin component of mononuclear particles having coating layers of a high fat content. Thus, an unpleasant flavor can be improved; a dissolution rate of the vitamin in water can be reduced; slow-release property can be provided, a reaction between the vitamin and other components can be inhibited; and properties of the resultant preparation can be improved.

In case of the coated water-soluble vitamin component, the β-form crystals to be used as the seed crystals in the present invention can be selected from the same coat material as described above and it crystal form is β-form. The β-form seed crystals can be prepared by melting lipid having the same fatty acid composition as that of the coat material or at least one coat material to be used and holding the melt at a predetermined temperature for predetermined time. For example, in case of hydrogenated soybean oil, the seed crystals can be prepared by holding its melt at 50 to 60° C. for 1 to 8 hours, preferably 4 to 6 hours after melting by heating to form β-form crystals.

Further, the β-form seed crystals to be used in the present invention may be a part of the coated water-soluble vitamin component produced in a different batch or run according to the above process. For example, among the coated water-soluble vitamin component produced, those having too small particle size and, in case of those having too large particle size, e.g., having particle size of not less than 2,000 μm, after pulverized can be used as the β-form seed crystals. The crystal form of the coated water-soluble vitamin component to be used as the seed crystals may be β-form, β'-form or a mixture thereof.

The seed crystals is added in an amount of 0.1 to 90% by weight, preferably 1 to 50% by weight, more preferably 1 to 30% by weight based on the total weight of the coated water-soluble vitamin component. The seed crystals can be added together with the core material or can be added when the coat material is added dropwise. Further, the seed crystals can be added after formation of the coating layer.

Any sweetener which can be used for improving a flavor can be used in the present invention. Sucrose can be used. Further, a sweetener selected from aspartame, potassium acesulfame, sucrarose, sodium saccharin and licorice extract (or glycyrrhizin). The amount of the sweetener is not specifically limited but, when the sweetener is added in an amount of 0.1 to 5.0% by weight based on the total weight of the vitamin preparation, excellent improvement of a flavor can be achieved together with improvement resulted from the coating of the water-soluble vitamin.

As the excipient, for example, there are monosaccharides, disaccharides, polysaccharides, hydrogenated products thereof (e.g., hydrogenated maltose, paratinit, sorbitol, mannitol, maltitol, erythritol, xylitol, lactitol etc.) and the like.

The water-soluble vitamin preparation of the present invention can be produced by compounding these coated water-soluble vitamin component with the sweetener, the excipient and, if necessary, other additives such as flavor, binder, lubricant and the like according to a per se known method to give a preparation in the form suitable for oral administration such as powders, granules, tablets or capsules.

The vitamin content of the vitamin preparation can be appropriately selected according to a particular use thereof.

Thus, according to the present invention, the coated preparation of a hydrophilic core material whose dissolution in water is inhibited can be obtained by a simple process only using a stirring-mixing device with preventing blocking between coated particles.

Even when the resultant coated preparation is soaked in water, dissolution of the core material is little and, therefore, such advantages that improvement of stability of the core material and prevention of flavor deterioration can be expected. According to a particular use of the, core material, the coated preparation can be utilized for stabilization of the unstable core material, control of the dissolution rate in water and reactivity (slow-release property) of the core material, control of flavor release of the core material (prevention of release of acid flavor, odor, etc.) and the like. For example, adverse influence due to low pH of an organic acid can be prevented. Further, instability of L-ascorbic acid by water, oxygen, metals and the like can be prevented and, on the other hand, influence of L-ascorbic acid on other components can also be prevented.

Moreover, the present invention can provide the water-soluble vitamin preparation useful as medicines and health food. In the water-soluble vitamin preparation of the present invention, an unpleasant flavor of a water-soluble vitamin is improved to reduce the unpleasant flavor in the mouth; a dissolution rate of a water-soluble vitamin in water is reduced to provide slow-release properties; reactions between components are inhibited; and preparation properties are improved.

The following Examples further illustrate the present invention in detail but are not to be construed to limit the scope thereof.

In the following Examples, the dissolution rate in water of the coated preparation was determined by the following method.

The preparation (about 200 mg) was weighed accurately in a 50 ml centrifuge tube with a plastic cap. To this was added 2% metaphosphoric acid (20 ml) and, after capping, the mixture was shaken (240 times/min., 40 mm wide for 60 minutes) with a vertical shaker (SW-11W manufactured by Taiyo Kagaku) and filtered (Toyo Filter Paper No. 2). The filtrate (10 ml) was taken into a 50 ml flask and the L-ascorbic content in the filtrate was determined by iodine method. This content was used as the dissolution amount. The dissolution rate of L-ascorbic acid was calculated on the basis of this dissolution amount of L-ascorbic acid.

The fat crystalline form of each preparation was confirmed by measuring the melting point.

L-ascorbic acid (average particle size 120 $\mu$m) was used as the core material and hydrogenated soybean oil was used as the coat material.

In the Examples, all the percents are by weight.

EXAMPLE 1

L-ascorbic acid was placed in a jacketed stirring-mixing device (Microspeed Mixer) and held at 50 to 55° C. To this was added dropwise hydrogenated soybean oil under conditions as shown in Table 1 to cover the L-ascorbic acid (30% coating). After coating, the coated material was stored in an incubator at 50° C. and the dissolution rates in water prior to and after storage were determined. Further, the fat crystalline forms prior to and after storage were determined.

The results are shown in Table 1.

TABLE 1

| Batch | 1 | 2 |
|---|---|---|
| L-ascorbic acid (g) | 7,500 | 7,500 |
| Hydrogenated soybean oil (g) | 3,200 | 3,200 |
| Addition of β-form crystal preparation (g) | 0 | 0 |
| Fat temperature (° C.) | 81–86 | 82–90 |
| Time required for dropping (min.) | 45 | 70 |
| Fat crystal form of preparation | | |
| After dropping | β' (all) | β' (almost) |
| After storage at 50° C. | β (after 35 hrs.) | β (after 21 hrs.) |
| L-ascorbic acid content (%) | 71.4 | 72.4 |
| Dissolution rate in water (%) | | |
| After coating | 17.8 | 20.1 |
| After storage at 50° C. | 43.9 | 35.2 |

As seen from Table 1, in the preparation obtained by 45 minute-dropping time (batch 1), all the fat crystal forms of the preparation after coating were β'-form. In the preparation obtained by 70 minute-dropping time (batch 2), almost all the fat crystal forms of the preparation after coating were still β'-form. This was considered to be resulted from failure to add β-form crystal preparation as seed crystals. When the preparation was stored in an incubator at 50° C. and the dissolution rate and caking were evaluated, the dissolution rate in water became faster than that prior to storage and was about 40%. Regarding the degree of caking, the preparation was in the form of lamps which were difficult to be crushed in a hand because the preparation had wider β'-form crystal area prior to storage and was required much transition energy.

Since the crystal form of the preparation of batch 1 was still a mixture of crystal forms containing a large amount of β'-form crystals even after storage at 50° C. for 17 hours, the storage was continued for 35 hours.

EXAMPLE 2

According to the same manner as that in Example 1, L-ascorbic acid was coated with hydrogenated soybean oil except that β-form crystal preparation (about 20% based on the total weight of the resultant preparation) was added and coating was carried out under the conditions shown in Table 2 to evaluate addition of seed crystals.

The resultant preparation (30% coating) other than that having particle size of more than 850 μm was used as seed crystals in the next batch to recycle the preparation.

In batches 3 and 4, the β-form seed crystals used were the preparations obtained in batches 1 and 2 which were pulverized by a power mill. In batch 5, the preparation obtained in batch 3 which had particle size of 850 μm or less was used as seed crystals to study pulverization of the preparation to be recycled as seed crystals.

The results are shown in Table 2.

TABLE 2

| Batch | 3 | 4 | 5 |
|---|---|---|---|
| L-ascorbic acid (g) | 7,500 | 7,500 | 7,500 |
| Hydrogenated soybean oil (g) | 3,200 | 3,200 | 3,200 |
| Addition of β-form crystal preparation (powder) Amount (g) | 2,000 | 2,000 | 2,000 |
| Fat temperature (° C.) | 78–85 | 76–85 | 77–83 |
| Time required for dropping (min.) | 70 | 45 | 45 |
| Fat crystal form of preparation | | | |
| after dropping | β' (less) | β' (less) | β' (less) |
| after storage at 50° C. | β (after 21 hrs.) | β (after 17 hrs.) | β (after 15 hrs.) |
| L-ascorbic acid content (%) | 69.9 | 71.2 | 70.7 |
| Dissolution rate in water (%) | | | |
| after coating | 18.2 | 17.0 | 13.8 |
| after storage at 50° C. | 29.5 | 26.1 | 18.8 |
| Particle size 850 μm or less (g) | 9,800 | 10,021 | 9,933 |
| Yield (%) | 77.2 | 78.9 | 78.2 |

As seen from Table 2, when the β-form crystal preparation was added in an amount of 20%, the amount of β'-form crystals was decreased after coating. In addition, the dissolution rate in water after storage at 50° C. was not higher than 20% in case of batch 5 where the β-form crystal preparation was added without pulverization (850 μm or less). The dissolution rates after storage at 50° C. in batches 3 and 4 where the β-form crystal preparations were added without pulverization were also lower than that of Example 1 and were about 29% and about 26%, respectively.

Regarding caking, all the batches hardly caked prior to storage and, after storage, no caking was observed.

As seen from batches 3 and 4, the time required for dropping of the coat material hardly influenced the dissolution rate.

EXAMPLE 3

According to the same manner as that described in Example 2, the fat was added dropwise to cover L-ascorbic acid except that the production conditions were varied, for example, the amount of the β-form crystal preparation to be added was decreased, the number of revolution of the stirring blades was increased and the fat dropping site was changed.

The conditions and results are shown in Table 3.

TABLE 3

| Batch | 6 | 7 | 8 |
|---|---|---|---|
| L-ascorbic acid (g) | 7,500 | 7,500 | 7,500 |
| Hydrogenated soybean oil (g) | 3,200 | 3,200 | 3,200 |
| Addition of β-form crystal preparation (powder) Amount (g) | 2,000 (β'-form mixed) | 2,000 | 2,000 |
| Fat dropping site | ¾ periphery from baffle | ¾ periphery from baffle | just behind baffle |
| Fat temperature (° C.) | 87–92 | 83–95 | 83–94 |
| Number of revolution of blades (rpm) | 167–170 | 247–256 | 167–170 |
| Time required for dropping (min.) | 45 | 45 | 45 |
| Fat crystal form of preparation | | | |
| after dropping | β' (less) | β' (less) | β' (less) |
| after storage at 50° C. | β (after 18 hrs.) | β (after 18 hrs.) | β (after 66 hrs.) |
| L-ascorbic acid content (%) | 71.1 | 71.9 | 69.8 |
| Dissolution rate in water (%) | | | |
| after coating | 17.6 | 19.6 | 16.9 |
| after storage at 50° C. | 20.0 | 23.4 | 19.4 |
| Particle size 850 μm or less (g) | — | — | 10,316 |
| Yield (%) | — | — | 81.2 |

Since it was considered that about 5% of the coated preparation prepared in the last batch could not recovered and remained in the mixer because of adhesion to the wall, as seen from Table 3, the amount of β'-form crystal preparation was estimated to be 500 g and β-form crystal preparation (1,500 g, after storage at 50° C., particle size 850 μm or less) was added together with L-ascorbic acid in batch 6 to carry out dropping of the fat to obtained the coated preparation. The dissolution rate in water after storage at 50° C. was about 20% and there was no substantial difference from that using only β-form crystal preparation (2,000 g).

In batch 7, for increasing the powder fluidization rate of the raw materials such as L-ascorbic acid and the like, the number of revolution was increased to 250 rpm. Then, quality of the coated preparation, in particular, influence on the dissolution in water was evaluated. As the current intensity was higher, the fluidization of the raw materials became more vigorous. However, the dissolution rate in water was about 20% and there was no substantial difference from the dissolution rate of batch 5, i.e., that at about 170 rpm.

The fat was dropped at the site about ¾ away from the baffled of the mixer in the previous batches. In batch 8, the dropping site was moved to just behind the baffle of the mixer because it was considered that the yield of the product could be increased by dropping the fat at the site where vigorous powder fluidization occurred. However, the yield was 81% and there was no substantial difference from that of batch 5 in which the fat was dropped at the site about ¾ periphery away from the baffle.

Content Determination of Batch 6

In batch 6, the mixture of 80% of L-ascorbic acid and 20% of the coated crystal preparation (30% coating) was coated with 20% of the coat material (fat) to obtained the coated preparation having 30% coating. Since it was considered that L-ascorbic acid content tended to be varied, samples were collected randomly to examine uniformity of the content.

The results are shown in Table 4.

As seen from Table 4, there was no substantial difference in the content.

TABLE 4

Number of sampling: 10

| Sample | 1 | 2 | 3 | 4 | 5 | 6 | 7 | 8 | 9 | 10 |
|---|---|---|---|---|---|---|---|---|---|---|
| Content (%) (%) | 72.4 | 70.5 | 70.6 | 71.0 | 70.8 | 71.4 | 70.6 | 71.0 | 70.4 | 71.9 |

Average 71.1%, Standard deviation 0.622

EXAMPLE 4

Sugarless Vitamin Preparation (1) Preparation of Coated Calcium L-Ascorbate (70% Content)

To calcium L-ascorbate (1 kg, average particle size 80 μm, manufactured by Takeda Chemical Industries, Ltd.) placed in a jacketed high speed fluid mixer (Microspeed Mixer manufactured by Fukae Kogyo) and warmed to 50° C. with stirring. The stirring was continued. To this was added a hot melt of hydrogenated soybean oil (melting point 68° C., 430 g) with stirring continuously at a rate of 10 g/min. to cover calcium L-ascorbate uniformly. Then, the resultant coated preparation was cooled to 40° C. to obtain the desired calcium L-ascorbate coated with the fat.

(2) Preparation of Sugarless Vitamin Preparation

According to the formulations shown in Table 5, sugarless vitamin tablets (0.4 g/tablet, calcium L-ascorbate 125 mg/tablet) were prepared under the following compression conditions.

Compression Conditions

Tablet machine: CLEANPRESS Correct 6HUK (manufactured by Kikushui Seisakusho)

Punch-mortar: 10 mmΦ, 8.5R

Compression: 1.0–3.0 t/cm²

TABLE 5

| Components | A Amount (%) | B Amount (%) |
|---|---|---|
| Vitamin B₁ nitrate | 0.060 | 0.060 |
| Vitamin B₂ (riboflavin) | 0.090 | 0.090 |
| Vitamin B₆ hydrochloride | 0.220 | 0.220 |
| Calcium L-ascorbate | 38.185 | 0 |
| Coated calcium L-ascorbate (70% content) | 0 | 54.566 |
| Nicotinamide (fine particles) | 1.050 | 1.050 |
| Calcium pantothenate 65% preparation | 1.050 | 1.050 |
| Folic acid | 0.030 | 0.030 |
| Hydrogenated maltose syrup | 55.115 | 38.734 |
| Fruit flavor powder | 3.000 | 3.000 |

TABLE 5-continued

| Components | A Amount (%) | B Amount (%) |
|---|---|---|
| Aspartame | 0.500 | 0.500 |
| Magnesium stearate | 0.700 | 0.700 |
| Total | 100.0 | 100.0 |

In Table 5, calcium pantothenate 65% preparation is "Calcium Pantothenate Type S" soled by Takeda Chemical Industries, Ltd.

The resultants tables A and B were subjected to organoleptic evaluation by 10 panelists (5 men, 5 women) to evaluate bitterness.

The results are shown in Table 6.

TABLE 6

| Tablet A | 9 panelists felt that A was bitter than B |
|---|---|
| Tablet B | 1 panelist felt that B was bitter than A |

As seen from Table 6, the tablet using uncoated calcium L-ascorbate had a bitter taste even if aspartame was used together. On the other hand, the tablet of the present invention using the coated calcium L-ascorbate had an improved taste.

The same improved flavor can be obtained by using paratinit, sorbitol, mannitol, maltitol, erythritol, xylitol or lactitol or a mixture thereof instead of hydrogenated maltose syrup in the formulation of Table 5. In addition, stevioside or potassium acesulfame can be used instead of aspartame. Further, scrarose can be used in ⅓ amount of aspartame.

EXAMPLE 5

Sugarless Vitamin Preparation (1) Preparation of Coated Calcium L-Ascorbate (90% Content)

To calcium L-ascorbate (5 kg, manufactured by Takeda Chemical Industries, Ltd.) placed in Microspeed Mixer (temperature controllable) was added hydrogenated soybean oil (0.5 kg) with stirring and warming up to 70° C. The mixture was held at the same temperature for 10 minutes and then slowly cooled to 62 to 64° C. by allowing it to stand. The mixture was further slowly cooled to 50° C. or lower by allowing it to stand to obtained the desired coated component.

(2) Preparation of Sugarless Vitamin Preparation

According to the formulation shown in Table 7, sugarless vitamin tablets (0.5 g/tablet, calcium L-acrobat 150 mg/tablet) were prepared under the following compression conditions.

Compression Conditions

Tablet machine: CLEANPRESS Correct 6HUK (manufactured by Kikushui Seisakusho)

Punch-mortar: 11 mmΦ, 8.5R
Compression: 1.0–3.0 t/cm²

TABLE 7

|  | A (%) | B (%) |
| --- | --- | --- |
| Calcium L-ascorbate | 30.00 | — |
| Coated calcium L-ascorbate (90% content) | — | 33.30 |
| Hydrogenated maltose syrup | 60.00 | 58.00 |
| Aspartame | 1.00 | 1.00 |
| Corn starch | 8.30 | 7.00 |
| Magnesium stearate | 0.70 | 0.70 |
| Total | 100.0 | 100.0 |

Regarding the tablets A and B obtained, bitterness was evaluated by 10 panelists (5 men and 5 women). After rinsing the mouth, each panelist tasted one tablet and evaluated intensity of the bitter taste.

As a result, ten panelists felt that tablet A was more bitter than tablet B, while there was no panelist who felt that tablet B was more bitter than tablet A.

This result also show clearly that the tablet using the coated calcium L-ascorbate has a more improved flavor.

In addition, when aspartame was replaced with potassium acesulfame, the same improvement of the flavor was achieved.

EXAMPLE 6

Each (0.4 g) of calcium L-ascorbate and the coated calcium L-ascorbate (70% L-ascorbate content) produced in Example 4 was filled in gelatin capsules (manufactured by Warner-Lambert Company, body volume 0.68 ml) and the capsules were placed in a transparent glass bottle. The bottle was sealed and stored in an incubator at 40° C. for 30 days to observe the change in appearances.

The results are as follows.

The capsules in which calcium L-ascorbate was filled caused severe browning. On the other hand, the capsules in which the coated calcium L-ascorbate (70% L-ascorbate content) hardly caused browning.

These results show that, when the coated calcium L-ascorbate is used, browning due to the reaction between L-ascorbic acid and the gelatin capsule is prevented. Thus, the use of the coated water-soluble vitamin component can prevent the reaction between components of the preparation.

What is claimed is:

1. A water-soluble vitamin preparation having an improved flavor which comprises a coated water-soluble vitamin, a sweetener and an excipient; and said coated vitamin obtained by coating a water-soluble vitamin core material having an unpleasant flavor with at least one coating layer of a coat material selected from hydrophobic hot-melt lipid which is formed by melting, adding and solidifying the coat material with fluidizing the core material, wherein the sweetener is at least one material selected from the group consisting of aspartame, potassium acesulfame, sucrarose, sodium saccharin and licorice extract.

2. The water-soluble vitamin preparation according to claim 1, wherein the sweetener content of the preparation is 0.1 to 5.0% by weight.

* * * * *